United States Patent [19]

Gupta

[11] 4,073,876

[45] Feb. 14, 1978

[54] PREPARATION OF GLYCOL ESTERS

[75] Inventor: Vijai P. Gupta, Freehold, N.J.

[73] Assignee: Halcon International, Inc., New York, N.Y.

[21] Appl. No.: 701,464

[22] Filed: July 1, 1976

[51] Int. Cl.$^2$ .................. C07C 67/05; C01B 19/00
[52] U.S. Cl. .................. 423/508; 260/287 G; 260/295 R; 260/295.5 R; 260/326.13 R; 260/347.5; 260/410.6; 260/465.4; 560/246; 560/178; 560/230; 560/187; 560/152; 560/112; 560/100; 560/20; 560/67; 560/50; 560/105; 423/509; 560/63; 560/124; 560/122; 560/1
[58] Field of Search .............. 260/497 R, 475 P; 423/508, 509, 510

[56] References Cited

U.S. PATENT DOCUMENTS

| | | | |
|---|---|---|---|
| 3,637,515 | 1/1972 | Huguet | 260/497 R |
| 3,715,389 | 2/1973 | Hoch | 260/497 R |
| 3,778,468 | 12/1973 | Kollar | 260/497 R |
| 3,872,164 | 3/1975 | Schmidt | 260/497 R |
| 3,907,874 | 9/1975 | Harvey | 260/497 R |
| 3,985,795 | 10/1976 | Kollar | 260/497 R |

FOREIGN PATENT DOCUMENTS 2,110,212   9/1971   Germany.

*Primary Examiner*—Lorraine A. Weinberger
*Assistant Examiner*—Michael Shippen
*Attorney, Agent, or Firm*—William C. Long; David Dick; Riggs T. Stewart

[57] ABSTRACT

In the preparation of glycol esters by the oxidation of an olefin in the presence of a catalyst comprising tellurium, wherein the accumulation of foreign metals in association with the tellurium catalyst component has an adverse effect upon the reaction, such foreign metals are maintained at low levels while the tellurium catalyst values are recovered for recycling in high yield by purging a portion of a high-boiling residual fraction produced in the distillation treatment of the reaction mixture and treating the purged portion with water and/or an aqueous alkaline solution.

3 Claims, 1 Drawing Figure

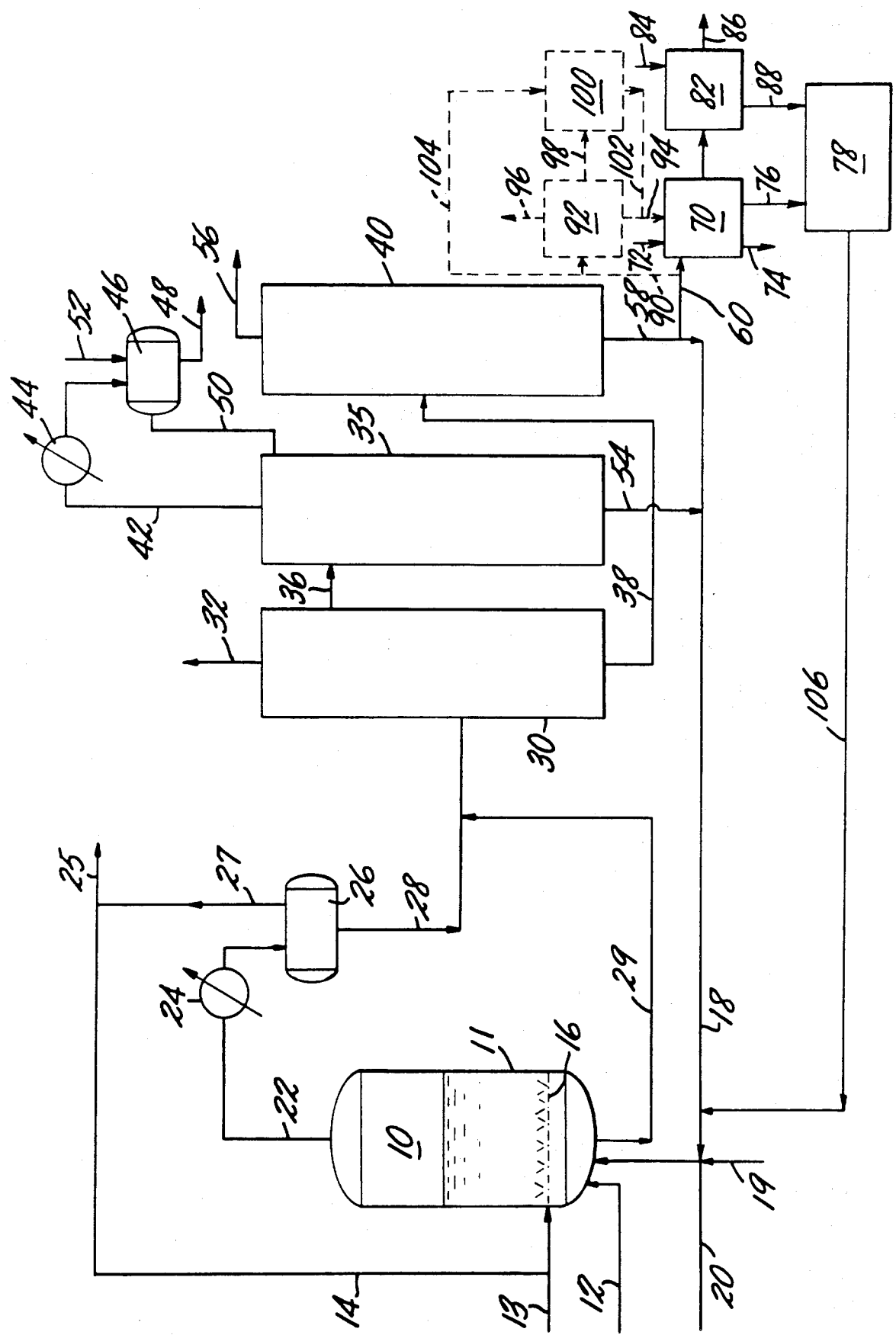

PREPARATION OF GLYCOL ESTERS

This invention relates to the preparation of glycol esters by the oxidation of an olefin with molecular oxygen in the presence of a carboxylic acid and in the presence of a tellurium catalyst, and is more particularly concerned with the recovery and recycling of the tellurium catalyst.

The preparation of glycol esters by molecular oxygen oxidation of olefins in a carboxylic acid medium using a tellurium catalyst has been described in numerous patents issued within the last few years, such as Kollar U.S. Pat. Nos. 3,668,239, 3,689,535, 3,743,672, and 3,778,468, Hoch et al U.S. Pat. No. 3,715,389, and Schmidt U.S. Pat. No. 3,872,164. In these processes, the reaction mixture from the oxidation step is treated in various ways to recover the product glycol esters and there is obtained a high-boiling residual fraction which contains tellurium values which can be reused in the oxidation. In the course of carrying out these processes, however, it has been found that various foreign metals, such as iron, chromium and nickel, and sometimes molybdenum, titanium, copper, and the like, are introduced into the system either as trace components in the raw materials supplied to the system or, more commonly, as the result of the corrosive effect of the reaction mixture and its components upon the materials of construction of the apparatus units which come into contact with the reaction components. While these metals are introduced in very minute quantities, when the processes are carried out continuously and the high-boiling residual fraction containing tellurium values is repeatedly recycled to the oxidation step, they gradually accumulate and in the course of time their quantity increases to the extent that they tend to have an adverse effect upon the oxidation reaction. Consequently, it is necessary to draw off a purge stream from the recycling high-boiling fraction in order to keep the quantity of these metals at a tolerable level. Purging of the recycle stream is also desirable in order to prevent the build up of high-boiling organic components of the reaction mixture. When the purge stream is drawn off, however, it contains not only the undesired metals and "heavy" organic materials but it also contains the valuable and useful tellurium catalyst and the effective recovery of the tellurium values for reuse in the reaction has heretofore presented a serious practical problem.

It is accordingly an object of this invention to provide an improved process for the preparation of glycol esters, wherein the recycling of undesired contaminating metals is minimized and the recovery of valuable tellurium values is effectively realized.

It is a further object of the invention to provide a process of the character indicated, wherein tellurium catalyst values are recovered in high yield from high-boiling purge streams containing such contaminating metals as well as high-boiling organic components formed in the ester-producing reaction.

Other objects and features of the invention will be readily apparent from the following detailed description of the invention.

In accordance with the invention, it has been surprisingly discovered that the tellurium values in a purge stream from the high-boiling residual fraction resulting from the distillation treatment of the reaction product produced by the molecular oxygen oxidation of an olefin in a carboxylic acid medium with a tellurium catalyst can be recovered in high yield by treating the purge stream with water and/or an aqueous alkaline solution. Preferably, the process comprises the use of both a treatment with water and a treatment with an aqueous alkaline solution.

In order to set the background for the invention and to facilitate its understanding, reference will be made to the type of process for producing glycol esters with which the process of the invention is advantageously employed. Thus, typical reaction systems which produce high-boiling, tellurium-containing fractions or residues from the purge streams of which foreign metals are removed and tellurium values are recovered in accordance with the invention are those derived from the production of mono- and di-carboxylate esters of vicinal glycols by the oxidation with molecular oxygen of an olefin in the presence of a carboxylic acid and in the presence of a catalyst system comprising a tellurium cation plus at least one of bromine, chlorine, a bromine-containing compound, or a chlorine-containing compound. Such catalyst sytems are disclosed, for example, in the above-mentioned U.S. patents and the disclosures of said patents are incorporated herein by reference. The following equations illustrate the primary chemical reactions involved, the oxidation of ethylene with molecular oxygen in the presence of an acetic acid being selected to facilitate the presentation.

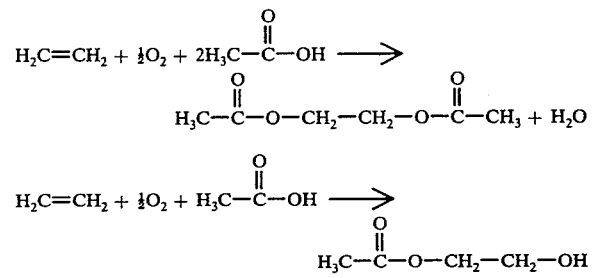

The illustrated reactions occur in the liquid phase within an oxidation zone containing a liquid phase reaction medium. The liquid-phase reaction medium contains the carboxylic acid, the ester products of the reaction, glycol precursors, reaction by-products, including water, as well as the catalyst system employed, dissolved olefin and dissolved oxygen also being present. Normally, the liquid reaction medium will contain from 30 to 90 weight percent of carboxylic acid, 5 to 60 weight percent of reaction products including glycol di-carboxylate, glycol mono-carboxylate, glycol precursors, and by-products. The term glycol precursors is used to define reaction products which, like the glycol carboxylates, are convertible to the corresponding glycol by hydrolysis, or are convertible into glycol esters, e.g., by recycling to the reaction zone, or by reaction with a carboxylic acid, i.e., they are compounds which embody a glycol moiety. Such precursors include the glycol itself, other esters, as well as halogenated compounds, the halogen being introduced into the system as a catalyst component. Illustrative halogenated precursors, assuming the halogen to be bromine, and assuming the olefin to be ethylene, include ethylene bromohydrin, 2-bromoethyl acetate, 1,2-dibromoethane and other brominated derivatives. The tellurium, expressed as Te, will generally be present in the amount of 0.2% to 4% by weight of the liquid reaction medium and the halogen values, expressed as Br or Cl, in the amount of 2% to 25% by weight. In addition to water, the principal by-products are CO$_2$ and CO, with minor amounts of other organic compounds, most of which are lower boiling than the esters, and high-boiling materials. This reaction mixture is separated into a plurality of fractions, and portions of all or some of these fractions, including high-boiling materials and catalyst components, are recycled to the oxidation zone. In accordance with the process of this invention, it is possible to achieve maximum conservation of the tellurium values, as will be discussed below.

The reaction is generally carried out continuously with a portion of the liquid phase reaction medium being continuously withdrawn from the oxidation zone and processed in the manner indicated. At the same time, olefin, carboxylic acid, and oxygen, together with recycle components are continuously introduced into the reaction zone. Thus, the liquid feed is composed primarily of carboxylic acid, e.g., 65 to 95 weight %, but is also comprises the catalyst components dissolved or suspended in it in amounts to provide the above-indicated concentrations in the reaction zone, and recycle materials such as glycol esters, e.g., 1 to 15 weight % and higher boiling materials, e.g., 1 to 20 weight %.

The molecular-oxygen-containing gas can be supplied in concentrated form, i.e., having an oxygen content of 85 mol % or more it can be supplied in the form of air or as enriched air or diluted air. The oxygen-containing gas and the olefin need not be specifically purified and can contain those impurities normally associated with them. For example, the olefin can contain normal quantities, e.g., up to 10 mol % of saturated hydrocarbons, e.g., ethane in the case of ethylene, and the oxygen can contain nitrogen, argon, etc.

The olefins useful in the process are preferably the alkenes, ar-alkenes, and cycloalkenes. Included among the alkenes are mono-alkenes, di-alkenes and tri-alkenes. Suitably, these alkenes have straight or branched chains containing from 2 to 30 carbon atoms. Illustrative alkenes include ethylene, propylene, butene-1, butene-2, 2-methyl-butene-2, pentene-1, heptene-2, octene-1, decene-1, tetradecene-1, pentadecene-1, hexadecene-1, pentacosene-1, and triacontene-1. In the di-alkenes the double bond may be conjugated or isolated and the carbon chain may be straight or branched and the olefin may contain up to 30 carbon atoms. The ar-alkenes contain an aromatic nucleus and at least one double bond. The di-alkenes are exemplified by 1,3-butadiene, 1,5-butadiene, 1,4-pentadiene, and 1,3-hexadiene. Examples of ar-alkenes are phenyl alkenes and di-phenylalkenes wherein the alkenyl side chain contains from 2 to 5 carbons, such as styrene, 2-methyl styrene and alpha-ethyl-beta-methyl styrene, and diphenyl alkenes such as 1,1-di-phenylethylene, 1,2-diphenyl propene and 2,3-diphenyl-but-2-ene. The cycloalkenes may contain from 5–12 carbon atoms such as cyclopentene, cyclopentadiene, cyclohexene, cyclodecene, and cyclododecene. All of the above alkenes, ar-alkenes and cycloalkenes may contain one or more functional substitutents which are inert to the reaction such as nitro, cyano, chloro, lower alkoxy (methoxy, propoxy), lower alkylthio (methylthio, butylthio) hydroxy, lower alkanoyloxy of 2–6 carbons (acetyloxy), and the like. Preferred are the lower alkenes containing 2 to 5 carbon atoms, especially ethylene, propylene and butene-2. The olefin may contain the variety of impurities normally associated with commercially available olefins, such as ethane in the case of ethylene and propane in the case of propylene.

The carboxylic acid employed in the oxidation supplies the ester moiety to the glycol ester and is suitably a mono-aliphatic acid of from 2 to 30 carbon atoms such as acetic, propionic, butyric, isobutyric, the valeric and caproic acids, as well as caprylic, capric and lauric acid, and higher mono aliphatic acids, such as myriatic, palmitic, stearic, hexacosanoic and tricosanoic acid. These mono aliphatic acids may be substituted, i.e., they may contain one or more functional substituents such as lower alkoxy (methoxy, propoxy), chloro, cyano, lower alkylthio (methylthio, ethylthio, butylthio), and the like. Preferably, any substitutents are inert under the oxidation conditions. Examples include acetoacetic, chloropropionic, cyanoacetic, methoxyacetic acid and 3-methylthiopropionic acid. Among the aromatic carboxylic acids may be mentioned benzoic, 1-naphthoic, o-toluic, m-toluic, o-chlorobenzoic, m-chlorobenzoic, p-chlorobenzoic, o-nitrobenzoic, m-nitrobenzoic, p-hydroxybenzoic, anthranilic, m-aminobenzoic, p-aminobenzoic, phenylacetic, 2,4-dichlorophenyloxyacetic, hydrocinnamic, and 2-phenylbutyric acids. The alicyclic monocarboxylic acids may contain from 3 to 6 carbons in the ring, both substituted and unsubstituted, such as: cyclopropanecarboxylic, cyclopentanecarboxylic and hexahydrobenzoic. The heterocyclic acids may contain from 1 to 3 fused rings both substituted and unsubstituted, and may contain at least one and less than 4 hetero atoms such as oxygen, sulphur or nitrogen. Examples of such acids are picolinic, nicotinic, 3-indoleacetic, furoic, 2-thiophenecarboxylic, quinolinic, 2-methylindole-3-acetic, 3-chloro furoic, and 4-nitronicotinic. The carboxylic acid is preferably a lower aliphatic acid, especially acetic acid. Mixed carboxylic acids in any desired ratio can also be used and it will be apparent that the acid may be recycle acid containing the impurities indigenous to the process. In the preferred embodiments the produced esters include the ethylene and propylene glycol diacetate, dipropionate, dibutyrate, diisobutyrate, divalerates and dicaproates, as well as the corresponding mono-esters.

The tellurium catalyst, if desired, may be provided in its elemental form and added to the oxidation zone as a fine powder or it may be supplied in any form which in the reaction medium under oxidation conditions will yield at least some soluble cations. For example, the tellurium source may be the carbonate, oxide, hydroxide, bromide, chloride, lower alkoxide, e.g., (methoxide), phenoxide, carboxylate, and the like. Preferably, the tellurium is in the form of its oxide, hydroxide or salt of the carboxylic acid, and most preferably, the oxide. Furthermore, the tellurium compound employed may contain impurities normally associated with the commercially available compounds, and need not be purified. The tellurium can also, of course, be in the form recovered from the purge stream in accordance with this invention.

The halogen source used in conjunction with the tellurium catalyst can be any compound capable of producing bromide or chloride ions in solution, under the oxidation conditions. For example, the bromine may be in the form of Br$_2$, hydrobromic acid, a tellurium bromide, an organic bromide, or a metal bromide, and the chlorine may be in the corresponding form. Suitable organic halides include all the bromide or chloride derivatives of the olefin being oxidized and the reaction products. For example, in the oxidation of ethylene with bromine these include but are not limited to 1,2-dibromoethane, ethylene bromohydrin, 2-bromo-ethyl carboxylate and other bromine-containing derivatives of ethylene including higher molecular weight ethers and the like. Similarly, in the oxidation of propylene, the organic bromides include 1,2-dibromopropane, propylene bromohydrin, 2-bromo-propyl carboxylate and other bromine-containing derivatives of propylene and including higher molecular weight ethers, and the like. The concentration of total tellurium cation present expressed in terms of equivalents of cation per equivalent of halogen can suitably vary from about 1:0.01 to about 1:100.

The temperatures maintained in the oxidation zone may vary from about 50° C to the bubble point of the liquid phase reaction mixture within the zone, with temperatures from about 90° to about 200° C being preferred. Total pressures within the oxidation zone can be sub-atmospheric, or super-atmospheric, with pressure up to about 5,000 psia or higher being operable. Pressures from about 15 psia to about 1,000 psia are normally desired.

While the mol ratio of oxygen to olefin fed to the system can be varied to assist in maintaining olefin liquid phase concentration, the mol ratio of oxygen to olefin is not critical and, therefore, any suitable ratios can be used. For example, such ratios as 1:1000 to 1:001 may be used. Of course, care should be taken to avoid formation of flammable mixtures.

Reaction time, i.e., residence time within the reactor, can vary widely. Flow rates are preferably adjusted so that the rate of formation of product, measured as rate of formation of glycol ester, is from about 0.1 to about 10.0 gm.—mols per liter of liquid phase reaction medium per hour.

As above indicated, the process of this invention is preferably applied to a continuous system in which the olefin and molecular oxygen reactant are continuously introduced to the oxidation zone and are continuously reacted therewithin. The carboxylic acid reactant normally is also fed continuously to the oxidation zone, and the liquid phase reaction medium is normally continuously withdrawn therefrom, the liquid phase reaction medium containing the desired ester products and their precursors along with the tellurium values and the contaminating metals. However, the carboxylic acid reactant can be introduced intermittently and the liquid phase reaction medium can be withdrawn intermittently. The reaction can conveniently be carried out in one reaction vessel although, if desired, the reaction can be carried out in two or more vessels connected in series.

In typical operation, there is withdrawn a gaseous effluent composed primarily of inert gases introduced with the oxygen, unreacted oxygen, unreacted ethylene, CO, $CO_2$, and minor amounts of vaporized normally-liquid components of the liquid reaction mixture. This gaseous effluent is suitably partially condensed in order to liquefy the condensible components, which may be combined with the liquid feed stream to the oxidation zone and the non-condensed component of the gaseous effluent is recycled to the oxidation zone where it is supplemented by makeup ethylene and oxygen-containing gas, or the effluent gases are recycled without condensation; condensation being employed only on the purge gas. Suitably, a purge is removed from the cycle gaseous stream to prevent the build-up of inert components. At the same time, there is withdrawn a liquid effluent which represents a portion of the liquid reaction medium and, in a continuous operation wherein there is a continuous introduction of a liquid feed, the liquid effluent may be an overflow stream taken at the desired liquid level in the reaction zone. This liquid effluent is then processed to recover product glycol acetates, to remove water and undesired organic by-products, and to provide recycle streams to be returned to the oxidation zone along with makeup carboxylic acid and makeup catalyst components, and the highest boiling of these recycle streams is utilized in providing the purge stream for treatment in accordance with the invention to eliminate undesired metals and recover and recycle tellurium values to a maximum extent, as will be pointed out as the description proceeds. Thus, in a typical system which is, however, given by way of illustration only and which is susceptible of considerable variation, as will readily be apparent to those skilled in the art, the product stream from the oxidation zone is subjected to vaporization, preferably in a fractional distillation zone, although flash vaporization may suitably be employed, to recover overhead the more volatile components of the mixture, including water, carboxylic acids, and some halogen-containing compounds, thus largely separated from the heavier components, which include glycol esters, some carboxylic acid, heavier halogen-containing compounds, non-volatile catalyst components, including tellurium, and the like. Suitably, the lighter fraction is then treated by azeotropic distillation for water removal as described in Kollar U.S. Pat. No. 3,743,672.

The heavier fraction from the foregoing distillations is then suitably subjected to further distillation to effect a separation of the product esters from the remainder of the heavier fraction, the product esters being taken as an overhead fraction and the heavier portion being withdrawn as a bottoms product.

In carrying out the foregoing distillations, any conventional apparatus may be used, such as continuous tray or packed columns, and the pressures and temperatures can be varied appropriately in conventional manner to achieve the desired separations.

Typically, the liquid product-containing effluent from the oxidation zone is separated as desired in Schmidt U.S. Pat. No. 3,872,164. As shown in the Schmidt patent, the heavier fraction withdrawn as bottoms product from the last distillation is suitably recycled to the oxidation zone, combined with heavier fractions from preceding distillations and with make-up carboxylic acid and catalyst components, as desired. In order, however, to prevent the accumulation or build-up of metallic contaminants and of high-boiling organic components, a purge is taken from the heaver fraction, the volume of the purge depending upon the quantity of metals and "heavy" organics present. Ordinarily, it is desirable to keep the quantity of such contaminating metals in the heavier fraction at a low value to minimize their influence and to remove any net "make" of the heavy organic materials. As previously mentioned, the contaminating metals may enter the system with the feed components which, as indicated, may be in their commercially-available form and fed directly without further purification, and the metals also may enter the system by reason of gradual corrosion of the metal surfaces with which the oxidation reaction mixture and its components come into contact during the course of the oxidation and during the subsequent processing of the reaction mixture. In a typical system, metals and/or alloys such as stainless steel, Monel, Hastelloy, titanium, and the like are employed as materials of construction, e.g., for reactors, piping, condensers and distillation columns and, as a result, the contaminating metals found in the heavier bottoms fraction from the distillation to remove product esters may contain as contaminants metals such as those previously mentioned, especially iron, chromium, and nickel. The rate of corrosion is extremely slow and at any one time very small quantities of the metals are introduced into the system but, in continuous operation with continuous recycling, these small quantities can in time accumulate to an undesired extent and, consequently, they must be purged in order to keep their quantity desirably within predetermined limits. The purge ordinarily takes place continuously but there may be an intermittent purge stream taken, if desired. In any case, since the heavier fraction contains substantially all of the tellurium catalyst values contained in the reaction product removed from the oxidation zone, all purge streams contain these tellurium values and they represent a significant loss if merely discarded. In general the purge stream will represent about 1% of the total heavier fraction but a greater or smaller purge may be taken, depending upon the specific composition of the fraction purged.

In a typical case, the heavier fraction may contain 10 to 80 wt. % of glycol esters, 2 to 50 wt. % of high-boiling materials, including halogenated compounds, 2 to 30 wt. % of tellurium values, expressed as Te, along with the contaminating metals which have accumulated by recycle. This composition is merely illustrative and is subject to wide variation depending upon the specific processing parameters employed, the materials of construction used, and the particular manner of carrying out the distillation. If the content of glycol esters is relatively high, the purge stream is advantageously concentrated, e.g., by vacuum distillation before it is subjected to the aqueous and/or alkaline extraction in accordance with the invention in order to increase the relative proportion of the tellurium and contaminating metals in the liquid treated. The more volatile components removed in this concentration are suitably returned to the system, e.g., by adding them to the heavy recycle stream, if desired.

Accordingly, the purge stream is treated with water or an aqueous alkaline solution, the purge stream is treated both with water and with the alkaline solution, the water treatment being employed first, followed by treatment with the alkaline solution. Surprisingly, the contaminating metals are in forms which dissolve in the treating media but, equally surprising, the tellurium does not, so that following the treatment the tellurium remains as a solid deposit which can be directly returned to the system, e.g., by addition to the heavy recycle stream going to the oxidizer. Ordinarily, the treatment in accordance with the invention is carried out intermittently even when a continuous purge stream is taken, i.e., the purge stream is allowed to accumulate until a readily-handled volume has been obtained and then the accumulated stream is treated.

In the treatment or extraction with water in accordance with the invention, 1 to 1000 volumes of water per volume of purge liquid is employed. While a single extraction of the purge liquid with water can be employed, preferably the extraction is carried out in a plurality of stages, e.g., with 2 batches of water. To effect the extraction, the purge liquid is diluted with the desired volume of water and shaken or agitated briefly, e.g., for 30 to 600 seconds and then allowed to settle into an aqueous phase and a precipitate. The aqueous phase is readily removed from the precipitate by simple decantation, although filtration can be employed if desired. The water can be of any desired temperature but preferably it has a temperature of at least 25° C for optimum effectiveness. The treatment or extraction with an aqueous alkaline solution is carried out in the same manner except that, if the alkaline solution treatment is preceded by an extraction with water, only the precipitate from the aqueous extraction is employed. The alkaline solution can be any aqueous solution having a pH greater than 7.0, the alkalinity being provided by any soluble alkaline agent such as ammonia, alkali metal hydroxides, e.g., sodium hydroxide, alkali metal carbonates, e.g., sodium carbonate, and the like. Preferably, the alkaline extracting solution has a pH of at least 9.0. Following the alkaline extraction, the residual product is preferably given a final wash with water, especially if an alkaline treating solution of a relatively high pH has been employed, although this is not absolutely necessary. The water extraction or the alkaline extraction is ordinarily sufficient in most cases but the two-step aqueous extraction-alkaline extraction sequence is preferably employed, especially if it is found that the purge liquid contains molybdenum.

The accompanying drawing is a schematic representation of an illustrative system in connection with which the process of this invention may be employed. The following description of the drawing will serve to provide a fuller understanding and explanation of the invention and its advantages. In the following discussion the reactants are ethylene, acetic acid and oxygen, and the catalyst system is assumed to be cationic tellurium and anionic bromine, the latter being conveniently supplied as hydrogen bromide. Continuous operation is assumed, although this invention is not so limited.

To oxidation zone 10, within which is maintained a liquid phase reaction medium 11, are fed ethylene via conduit 12, oxygen via conduit 13 and the recycled vapor stream via conduit 14. While only the recycled vapor and oxygen-containing gas are shown as introduced through a sparger 16, all gaseous materials would normally be introduced in similar fashion. Mechanical agitating equipment (not shown) can be provided if desired.

Also introduced to oxidation 10 is a recycle liquid stream to be described below, which is fed through line 18. Combined with the recycle liquid stream are make-up acetic acid (via conduit 19) and make-up catalyst (e.g., tellurium oxide and HBr) through line 20. As shown, the make-up catalyst is suitably suspended or dissolved in the recycle liquid stream and the make-up acetic acid is also added to this stream before it enters the oxidation zone. Although the other feeds are preferably continuously fed to the oxidation zone, make-up acetic acid and/or make-up catalyst can readily be introduced intermittently, if desired.

Vapor comprising unreacted ethylene and oxygen together with gaseous by-products and diluents and more volatile components of the liquid phase reaction medium is withdrawn from oxidation zone 10 via conduit 22 and partially condensed in cooler 24. Condensed liquid and uncondensed vapor are separated from each other in separator 26. As shown, the condensed liquid is withdrawn from separator 26 through line 28, and a small quantity of this vapor may be purged via line 25 in conventional manner. The balance of the vapor is the recycled vapor stream returned to oxidation zone 10 via conduit 14.

A portion of the liquid-phase reaction medium is withdrawn from the oxidation zone 10 by means of line 29 and is fed to distillation zone 30. Within distillation zone 30 a volatile fraction comprising water, acetic acid, and components more volatile than the product esters are separated from a residual fraction comprising the product esters and less volatile and non-volatile components, and the volatile fraction is, in turn, separated into low-boiling constituents and an acetic acid-water fraction which may also contain close-boiling components such as halogenated, e.g., brominated, compounds.

As seen in the drawing, the low-boiling constituents which are more volatile than the acetic acid-water fraction are withdrawn through line 32, the acetic acid-water fraction is passed into azeotropic distillation zone 35 through line 36 and the residual fraction comprising the product esters is withdrawn through line 38 and passed to product distillation zone 40. The light components removed as vapor from the top of distillation zone 30 through line 32 may be discarded or they may be treated to recover individual components or they may be condensed and combined with the recycle liquid stream flowing through line 18 back to the oxidation zone. These several options are not illustrated but their application will be readily apparent to those skilled in the art. The aqueous acetic acid fraction is subjected in zone 35 to azeotropic distillation in the presence of an azeotroping agent which forms a minimum boiling azeotrope with water and the vapor overhead from azeotropic distillation zone 35, which consists almost exclusively of water and azeotroping agent, passes through line 42 into condenser 44 and the condensate is then separated in separator 46 into an aqueous phase which is discarded through line 48 and an organic phase composed primarily of the azeotroping agent which is returned as reflux through line 50 to azeotropic distillation zone 35. Make-up azeotropic agent is suitably added as required through line 52, communicating with separator 46. The non-vaporized fraction of the feed to azeotroping zone 35 is withdrawn through line 54 and mixed with recycle stream in line 18. In product separation zone 40, the residual glycol acetate-product-containing fraction composed primarily of product glycol acetates which, after removal by distillation of any halogenated compounds which may be present, can be used as such, e.g., as solvents or plasticizers or can be subjected to further treatment, for example, hydrolysis with water to yield ethylene glycol, or pyrolysis to yield vinyl acetate, as described, for example, in Kollar U.S. Pat. No. 3,689,535. A heavier fraction composed of higher-boiling constitutents and non-volatile components, including components of the catalyst system, are withdrawn from distillation zone 40 through line 58. This is the stream from which, in the embodiment illustrated, a portion is withdrawn through line 60 and is treated by the process of the invention, the remainder forming a recycle stream which enters line 18 for return to oxidation zone 10.

As seen in the lower right-hand portion of the drawing, line 60 leads to a first extraction zone 70 into which the treating solution is introduced through line 72, in one or a plurality of stages, and the aqueous phase resulting from the extraction and containing the contaminating metals is withdrawn through line 74. At the same time, the precipitate which contains substantially all of the tellurium values is passed through line 76 to a storage zone 78. When both a water extraction and an aqueous alkaline extraction are employed, the precipitated material, instead of being sent to zone 78, is passed through line 80 to extraction zone 82, into which the alkaline treating solution is introduced via line 84. The aqueous alkaline phase resulting from the extraction is then withdrawn through line 86 and the precipitate is passed through line 88 to zone 78. As previously mentioned, in the preferred embodiment of the process, the precipitate, after the alkaline treatment in zone 82, is subjected to final water extraction. This may take place in zone 82 or the precipitate may be transferred to a separate treating zone (not shown) for this aqueous treatment before being sent to zone 78. As also pointed out above, the purge stream in line 60 may be concentrated and/or accumulated prior to being passed to treatment zone 70. Thus the purge stream passes through line 90 to concentration zone 92 and the concentrated stream is led to treating zone 70 via line 94, the volatile material being withdrawn through line 96. In a typical case, the concentration is effected by a flash distillation, e.g., at a pot temperature of 100 to 225° C and a pressure of 5 to 5000 mmHg. If the concentrated stream is to be first accumulated it is led through line 98 to storage or accumulation zone 100, and it is eventually fed to treating zone 70 by way of line 102. If the purged stream is to be accumulated without concentration, line 104 leads it directly to zone 100. Finally, the recovered tellurium-rich precipitate is returned to the purge system, e.g., via line 106 which is illustrated as communicating with recycle line 18 containing the high-boiling recycle stream and the remainder of the tellurium being returned to the oxidizing zone 10.

It will, of course, be understood that the process of this invention is not limited to the treatment of a metal-contaminated tellurium-containing fraction produced in any specific manner. The oxidation may be carried out under different conditions to produce a reaction mixture of different composition, the separation of the reaction mixture may be effected by different distillation sequences, or under different distillation conditions, as will be obvious to persons skilled in the art, and the heavy residual fraction may contain organic components of different types. As an example of a distillation operation different from that illustratively shown in the drawing, the distillation in zone 30 may be conducted to produce a residual fraction and the feed to zone 40 may be a side-stream from the lower portion of zone 30. In this case a purge from the residual fraction from zone 30 alone, or combined with the residual fraction from zone 40, can be treated by the process of the invention. Moreover, it should be emphasized that the "purge" stream treated may range from a small to a relatively large percentage of the residual fraction, as desired, possibly even the entire residual fraction.

The invention will be further understood by reference to the following examples which are given for illustrative purposes only and are not intended to be limitative of the invention.

EXAMPLE 1

Ethylene is oxidized in the presence of acetic acid in an apparatus comprising a 7.5 liter jacketed autoclave, with a draw-off conduit arranged to maintain a 3.9 liter liquid volume within the autoclave, employed. The autoclave is initially filled to the designated liquid level with a slurry of tellurium dioxide (1% calculated as Te) and hydrogen bromide (12%) suspended and/or dissolved in glacial acetic acid. The autoclave is then heated under nitrogen to 145° C. and ethylene and oxygen feeds are commenced at rates so as to maintain an 8% concentration of each of the effluent gases from the oxidation zone. Gas withdrawn from the autoclave is recycled through stainless-steel lines at a rate of 7,000-8,000 std. 1/hr. for admixture with the fresh gaseous reactants supplied, while a portion is purged to control buildup of by-product gases ($CO+CO_2$). Pressure is maintained at 400 psig by regulating this rate of gas withdrawal. The recycling gas is cooled to 20° C. in a stainless-steel condenser to recover the acetic acid contained therein. Liquid-phase reaction medium is withdrawn as it exceeds the designated level and is first vacuum distilled at a reboiler temperature of about 140°-165° C (60-85 mmHg) to obtain an overhead fraction composed primarily of water, acetic acid, and lower-boiling materials, a side stream comprising acetic acid, glycol esters and esterified ethers, some higher-boiling components, and a residue fraction comprising higher-boiling materials, including non-volatile catalyst values, plus glycol esters. The side stream fraction is fractionally distilled in an Oldershaw column containing 10 trays below the feed tray and 25 trays above the feed tray. The column is operated at atmospheric pressure with a bottoms temperature of about 210°-230° C to separate most of the glycol esters and the lower-boiling materials as overhead suitable for eventual recovery, and to provide a bottoms fraction of the higher-boiling materials plus some of the glycol esters. The bottoms fractions from both distillation units which comprise the higher-boiling materials, non-volatile catalyst components, and minor amounts of glycol esters, are combined to form a single heavy bottoms fraction. This fraction, after make-up acetic acid and bromine values (as HBr) are added to it provides a liquid feed stream which is supplied at a rate sufficient to maintain a constant draw-off stream of liquid-phase reaction medium, the withdrawal rate corresponding roughly to a three-quarter hour residence time.

After about 48 hours of continuous operation in the manner described above, during which samples are periodically taken and analyzed to ascertain composition, steady-state operation is achieved. Notwithstanding the prolonged period of operation, the rate of stainless-steel corrosion is so low and any metallic contamination of raw materials is so slight that there is no significant quantity of foreign metals in the recycle stream at this point. Accordingly, in order to simulate conditions which would exist after many multiples of the above-indicated operation, the recycle feed to the autoclave is augmented by the addition of small quantities of iron, chromium, nickel, and molybdenum, the introduction of these metals being facilitated by supplying them as ferrous bromide, chromium hydroxide, nickel bromide and molybdenum oxide, in amounts such that the heavy bottoms fraction after an additional 48 hours of operation contains per 100 parts, 0.23 part Fe, 0.0112 part Cr, 0.53 part Ni and 0.1 part Mo, this heavy residual fraction also containing 9.2 parts of tellurium.

Fifty parts by weight of a purge stream from the above-mentioned heavy bottoms fraction are mixed with 100 parts by weight of water at 80° C., agitated for about 15 minutes and then filtered. The precipitate recovered from the filtration is mixed with a further 100 parts of water at 80° C, agitated for about 10 minutes and filtered. The filtrate from the two extractions are combined and analyzed. They are found to contain 0.007 part chromium, 0.093 part iron, 0.215 part nickel, 0.0054 part molybdenum and 0.43 part tellurium. This shows that more than 90% of the tellurium remains in the precipitate for recycling to the reaction and that it is essentially free of chromium and contains less than 20% of the iron and nickel contained in the fraction treated. The molybdenum is removed to the extent of about 11%. When the experiment is repeated without the addition of molybdenum, a substantially foreign metal-free precipitate is obtained.

EXAMPLE 2

In a second experiment, the procedure of Example 1 is repeated except that the extracting medium is water to which sodium hydroxide has been added to increase its pH to 9.0. Analysis of the filtrates from this experiment shows that the precipitate contains more than 97% of the tellurium present in the treated fraction, none of the molybdenum, and only about 28% of the chromium. About half of the nickel is still present as is more than 95% of the iron. When the experiment is repeated without the addition of iron, to simulate corrosion from some non-ferrous alloys, no molybdenum is present and the amounts of chromium and nickel are substantially as indicated so that the precipitate contains substantially less than half of the foreign metals initially present and a very high percentage of the desired tellurium (97%).

EXAMPLE 3

In another set of experiments, the procedures of Examples 1 and 2 are combined, i.e., the precipitate from the sample containing the added iron, chromium, nickel and molybdenum, subjected to extraction with water as described in Example 1 is subjected to extraction with alkaline solution of pH9 as described in Example 2. The solid precipitate recovered from the alkaline extraction is found to comprise more than 88% of the tellurium initially present, no chromium, no molybdenum, and only about 17% of the iron and 11% of the nickel contained in the fraction treated.

In like manner other contaminating metals such as copper and manganese which may result from the corrosion of some alloys, and titanium which may result from the corrosion of titanium cladding, are effectively removed by extraction as described in Examples 1, 2 and 3.

What is claimed is:

1. A process for recovering tellurium values and removing contaminating metal components from a high-boiling tellurium-containing fraction obtained from the liquid reaction product produced in the manufacture of glycol esters by the molecular oxygen oxidation of an olefin in the presence of a carboxylic acid and a tellurium catalyst and containing contaminating metals in addition to the tellurium values, said high-boiling fraction comprising the highest boiling fraction produced by distillation of said liquid reaction product to recover the glycol esters therefrom, which comprises treating at least part of said fraction with water and/or an aqueous alkaline solution to produce an aqueous phase containing said contaminating metals and a precipitate containing substantially all of the tellurium values present in said fraction, and separating said precipitate from said aqueous phase.

2. A process as defined in claim 1, wherein said fraction is first treated with water and the precipitate from said treatment with water is treated with an aqueous alkaline solution.

3. In the preparation of glycol esters by the molecular oxidation of an olefin in the presence of a carboxylic acid and a tellurium catalyst, wherein the liquid reaction product is distilled to separate its components and to separate product glycol esters and wherein a high-boiling residual fraction containing the tellurium values is obtained, said high-boiling fraction comprising the highest boiling fraction produced by distillation of said liquid reaction product to recover the glycol esters therefrom, and said high-boiling fraction containing contaminating metals in addition to said tellurium values, the improvement which comprises treating at least part of said high-boiling fraction with water and/or an aqueous alkaline solution to produce an aqueous phase containing said contaminating metals and a precipitate containing substantially all of the tellurium values present in said fraction, and separating said precipitate from said aqueous phase.

* * * * *